United States Patent [19]
Goble

[11] Patent Number: 5,147,362
[45] Date of Patent: Sep. 15, 1992

[54] ENDOSTEAL LIGAMENT FIXATION DEVICE

[76] Inventor: E. Marlowe Goble, 850 E. 1200 North, Logan, Utah 84321

[21] Appl. No.: 681,974

[22] Filed: Apr. 8, 1991

[51] Int. Cl.$^5$ ................................................ A61F 2/08
[52] U.S. Cl. ..................... 606/72; 606/151; 623/13
[58] Field of Search .............. 606/60, 72, 76, 86, 606/88, 151, 154, 155; 623/13

[56] References Cited

U.S. PATENT DOCUMENTS

| | | |
|---|---|---|
| 4,301,551 | 11/1981 | Dore et al. . |
| 4,537,185 | 8/1985 | Stednitz . |
| 4,550,449 | 11/1985 | Tunc ................................ 606/60 X |
| 4,590,928 | 5/1986 | Hunt et al. ...................... 606/72 |
| 4,605,414 | 8/1986 | Cxajka . |
| 4,744,793 | 5/1988 | Parr et al. . |
| 4,772,286 | 9/1988 | Goble et al. . |
| 4,834,752 | 5/1989 | Van Kampen .................. 623/13 |
| 4,870,957 | 10/1989 | Goble et al. . |
| 4,927,421 | 5/1990 | Goble et al. . |
| 4,950,270 | 8/1990 | Bowman et al. . |
| 4,960,420 | 10/1990 | Goble et al. ................. 606/151 X |
| 4,988,351 | 1/1991 | Paulos et al. ................. 606/72 |
| 4,997,433 | 3/1991 | Goble et al. . |

Primary Examiner—Robert A. Hafer
Assistant Examiner—Sam Rimell
Attorney, Agent, or Firm—M. Reid Russell

[57] ABSTRACT

An endosteal ligament fixation device for mounting to a bone end of a bone tendon bone graft for use as a replacement anterior or posterior cruciate ligament. The endosteal ligament fixation device consists of a disk, collar, ring or band that is arranged to be fitted and secured to the graft bone end that includes a number of radially equidistant spaced outwardly projecting resilient barbs or pins extending therefrom, or may involve forming radially equidistantly spaced slanted holes into the graft bone end for mounting individual resilient barbs or pins. The barbs or pins can be sharp, blunt, or otherwise configured to extend into and to hold securely within a bone endosteum. A number of which barbs or pins are set radially into the disk, collar, ring or band, or individually into the bone end so as to be angled to extend off of and are spaced apart from the bone end surface, pointing towards the tendon coupling with that bone end. The barbs or pins are to individually flex inwardly during passage along the ligament tunnel wall when the graft bone end is urged therealong. At the tunnel end, the resilient barbs or pins are to flex outwardly into the bone endosteum, seating the graft bone end therein, and will fully extend into the bone endosteum when a tensile force is applied to the graft.

15 Claims, 4 Drawing Sheets

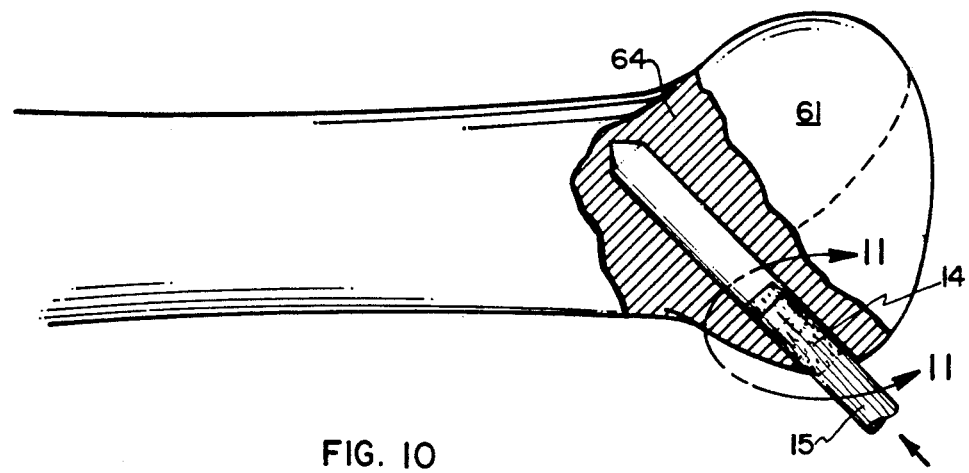
FIG. 10
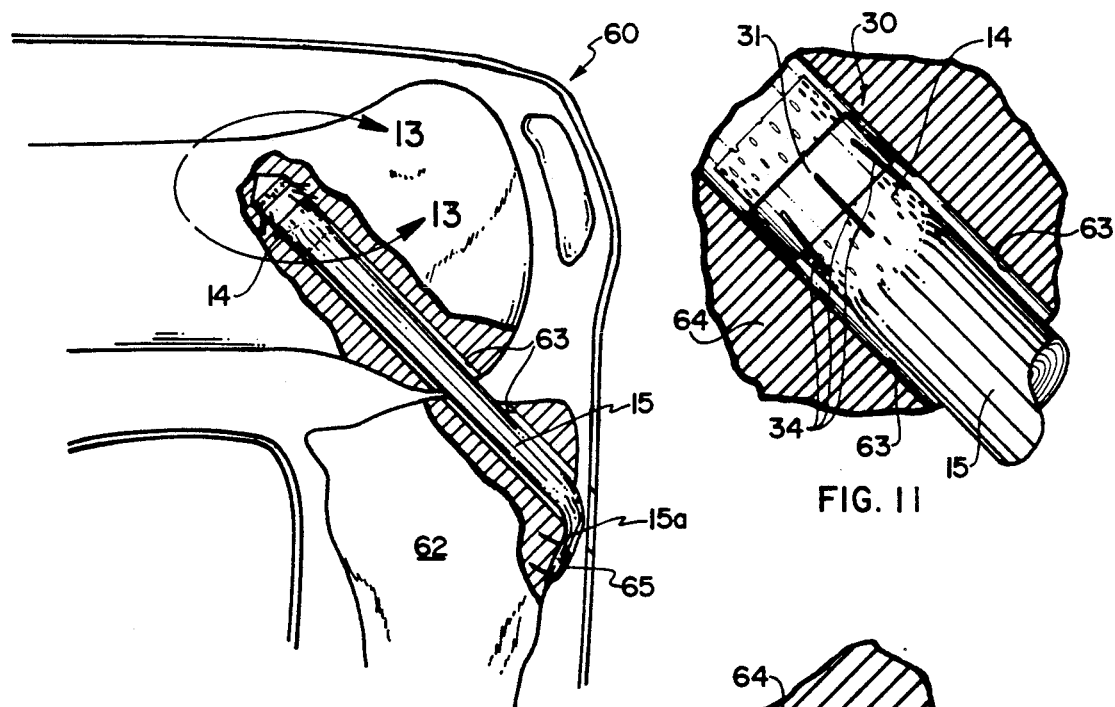
FIG. 11
FIG. 12
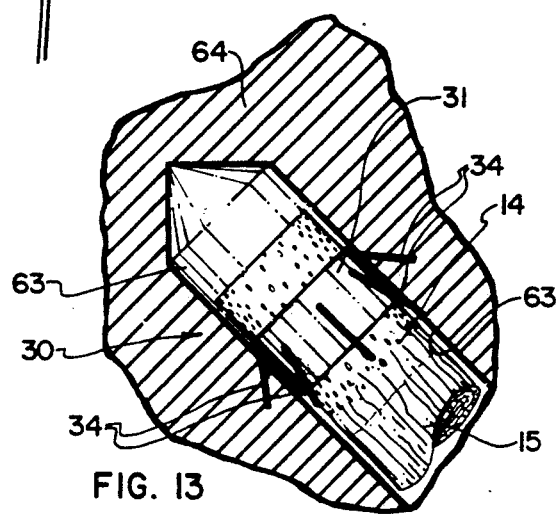
FIG. 13

ENDOSTEAL LIGAMENT FIXATION DEVICE

BACKGROUND OF THE INVENTION

1. Field of the Invention

This invention relates to ligament fixation devices and in particular to endosteal fixation arrangements for use with bone tendon bone grafts for use as replacements for an anterior or posterior cruciate ligament.

2. Prior Art

In recent years a number of systems and apparatus have been developed for use in arthroscopic surgical procedures involving repair or replacement of knee anterior or posterior cruciate ligaments. The present inventor is the inventor or joint inventor of a number of such systems, including a number of endosteal systems. Specifically, the applicant is the coinventor of U.S. Pat. No. 4,772,286, in a first or pioneer endosteal ligament anchor system, that was followed by U.S. Pat. Nos. 4,870,957 and 4,997,433, and a method patent, U.S. Pat. No. 4,927,421, all of which involve endosteal ligament anchor arrangements. Also, a currently pending U.S. patent application, Ser. No. 07/511,761, entitled "Endosteal Ligament Retainer and Process", is a further ligament anchor system. Unlike the present invention, none of which earlier endosteal ligament attachment arrangements teach or anticipate an arrangement for fitting a plurality of flexing barbs or pins to extend outwardly from a bone end of a bone tendon graft that is for installation, as a ligament replacement into a prepared ligament tunnel, the barbs or pins for flexing into a bone endosteum at the tunnel end endosteally locking that bone end therein.

Additional endosteal fixation device arrangements are shown in U.S. Pat. Nos. 4,537,185, to Stednitz and 4,950,270 to Bowman, et al, both showing a set screw mounting; with U.S. Pat. Nos. 4,301,551 to Dore, et al, and 4,744,793, to Parr, showing wedge type ligament mounting arrangements, and a patent to Czajka U.S. Pat. No. 4,605,414 shows a bone wedge anchor arrangement. None of which involve an endosteal mounting for securing flexing barbs or pins to a bone end of a bone tendon bone graft that is like that of the present invention.

BRIEF SUMMARY OF THE INVENTION

It is therefore a principal object of the present invention in an endosteal ligament fixation device to provide a device for endosteally securing a bone end of a bone tendon bone graft within a prepared anterior or posterior cruciate ligament tunnel that is formed through the ligament points of origin.

Another object of the present invention is to provide, as an endosteal ligament fixation device, an arrangement for fitting spaced barbs or pins into or onto a bone end of a bone tendon bone graft to extend therefrom and to flex into a bone endosteum for mounting which graft bone end therein.

Another object of the present invention is to provide, as a mounting arrangement for the endosteal ligament fixation device, a disk, collar, ring, or band arranged for sliding over or encircling the bone graft end that includes one or more holes or eyelets formed therein for receiving a fastener that is fitted into the graft bone end.

Another object of the present invention is to provide, with the disk, collar, ring or band, a number of flexing barbs or pins fitted thereto to extend in spaced relationship therearound, which barbs or pins, when compressed, flex individually to approximately the plane of the surface of the disk, collar, ring or band during travel into a ligament tunnel and are resilient to flex outwardly, into the bone endosteum, when fully installed.

Another object of the present invention is to provide with the disk, collar, ring or band, a number of barbs or pins fitted thereto to extend in equidistant spaced relationship therearound so as to project outwardly from the disk, collar, ring or band to a maximum angle that is less than sixty (60) degrees to the vertical from the bone surface when relaxed, and, when compressed as during graft travel in the ligament tunnel, are flexed inwardly to engage the bone end surface.

Still another object of the present invention is to provide, as the mounting arrangement, a collar or ring having a length adjustment capability for encircling and mounting to a bone end of a bone tendon bone graft.

Still another object of the present invention is to provide, by appropriately forming slanted holes in the bone end surface, for individually receiving a plurality of resilient barbs or pins at equidistant spaced intervals therearound as the endosteal ligament fixation device of the present invention.

Still another object of the present invention is to provide an endosteal ligament fixation device that is easily and reliably installed onto a bone end of a bone tendon bone graft for use in an anterior or posterior ligament replacement surgical procedure, the graft for installation into a ligament tunnel to anchor that graft bone end in the bone endosteum at the tunnel end against an applied tensile force.

The endosteal ligament fixation device of the present invention is for use with a bone tendon bone graft and consists of a mounting that is a disk, collar, ring or band for fitting to a bone end of the bone tendon graft, or consists of forming appropriate slanted holes in the graft bone end. Which graft is for installation into a prepared ligament tunnel in a ligament replacement surgical procedure. The disk, collar, ring or band mount includes, or the slanted holes formed in the bone end are to receive, plurality of barbs or pins that are spaced equidistantly and extend radially therefrom. Each of which barbs or pins are sufficiently resilient to fold against, or to approximately against, the surface of the bone end during graft installation in the prepared ligament tunnel. Each barb or pin is to flex outwardly into a bone endosteum at the tunnel end when a tensile force is applied to the graft free end.

The preferred barbs or pins are thin resilient wire whiskers that are fixed to extend radially outwardly from the disk, collar, ring, band, or bone end surface, and are individually angled at less than sixty (60) degrees, and preferably at approximately thirty (30) degrees, vertically relative to the bone end surface. The barbs or pins are resilient to bend so as to essentially flatten against the bone end surface during installation and will flex outwardly into the bone endosteum, when the graft is seated. Similarly, spaced slanted holes can be formed into the graft bone end to each receive a barb or pin therein, which barb or pin can be held therein as by an adhesive or the like, functioning as described above.

The disk can also be formed as a cap. Which disk or cap is centerholed, with the mounting collar or ring including one or more holes or tabs with holes. Each such hole is for receiving a mounting device, such as a screw, fitted therethrough and turned into the graft bone securing the mounting thereto. Further, more than one collar or ring can be fitted around the graft bone end. Which graft bone end can also be grooved therearound to accommodate one or more such collars or rings. Both the collar and ring can be formed to be length adjustable as by breaking it into a belt of a length for wrapping around the graft bone end, and with holes formed therethrough for receiving fasteners for securing the collar or ring ends to that graft bone end.

In practice, at least a pair of equidistantly spaced barbs or pins are mounted to the graft bone end, which barbs or pins are selected to remain seated in the bone endosteum under an applied tensile of stress of up to eighty (80) pounds, applied through the graft.

DESCRIPTION OF THE DRAWINGS

In the drawings that illustrate that which is presently regarded as the best modes for carrying out the invention:

FIG. 10 is a side elevation view of a distal femur showing a section removed to expose a ligament tunnel formed therein that terminates in the bone endosteum, and showing a bone end of a bone tendon bone graft being fitted therein as a replacement ligament, the bone end shown as mounting an endosteal ligament fixation device like that shown in FIG. 3, that includes a collar with the barbs or pins extending therefrom that are shown flexed inwardly by contact with the tunnel wall;

FIG. 11 is an expanded sectional view taken within the line 11—11 of FIG. 10;

FIG. 12 is a side elevation view of the patient's knee of FIG. 10 showing sections of the distal femur and proximal tibia removed to expose a ligament tunnel formed from the tibia cortex into the femur endosteum and showing the bone tendon bone graft and endosteal ligament fixation device of FIG. 10 fully fitted therein, the endosteal ligament fixation device barbs or pins shown as having flexed or flared outwardly into the femur endosteum; and FIG. 13 is an expanded sectional view taken within the line 13—13 of FIG. 12.

DETAILED DESCRIPTION

Figure 1:
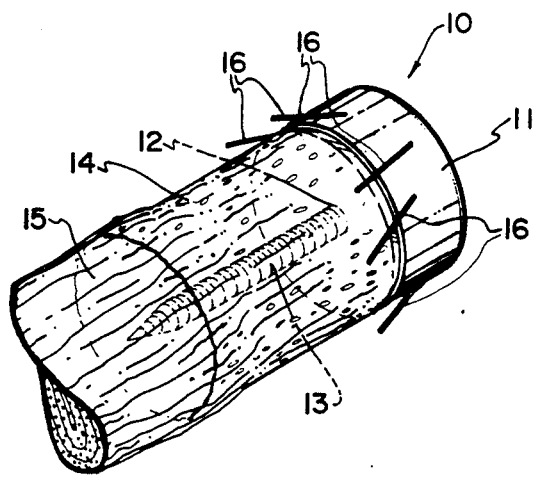
FIG. 1 is a side elevation perspective view of a bone end of a bone tendon bone graft that is to serve as a ligament and includes an embodiment of an endosteal ligament fixation device of the present invention shown as a disk that is mounted across the bone end top, from which disk a number of barbs or pins are shown to extend radially therearound and are angled from the disk cylindrical surface to be offset above the bone surface whereto the disk is installed.

In FIG. 1 is shown a first embodiment of an endosteal ligament fixation device 10 for a bone tendon bone graft, hereinafter referred to as "fixation device". The fixation device 10, as with all the endosteal ligament fixation device embodiments, is for arrangement with a bone end of a bone tendon bone graft, for endosteally securing that graft bone end in an end portion of a prepared ligament tunnel. FIGS. 10 through 13 show such a bone tendon bone graft being endosteally mounted utilizing an endosteal ligament fixation device of the present invention. Which figures illustrate an anterior cruciate ligament replacement procedure where tunnels are formed from the tibial cortex, at the tibial tuberosity, through both the femoral and tibial points of ligament origin and into the femur endosteum. This procedure and a description of each of the endosteal ligament fixation devices are set out in detail below.

Fixation device 10, as shown in FIG. 1, is arranged as a cylindrical disk 11 that is center tapped at 12, shown in broken lines, to receive a screw fastener 13, shown in broken lines, that is turned therethrough and into a head end top surface of a bone end 14. Which bone end, in turn, is attached during manufacture to tendon 15, forming the ligament replacement graft. A number of spaced barbs or pins 16, hereinafter referred to as "pins", are shown in a relaxed state extending outwardly from around the surface of disk 11. Each of which pins is angled from that disk surface so as to extend over and be spaced off from the bone end 14 surface. Which angles of each pin 16, in its relaxed state, relative to the bone end 14 surface, is less than sixty (60) degrees and is preferably approximately (30) degrees. While such pin 16 angles may be uniform for each pin, they may also be different from one to another within the scope of this disclosure.

The pins 16 are resilient to bend or depress towards the bone end 14 surface during graft installation, as illustrated in FIGS. 10 and 11, and will flex or spring outwardly into the bone endosteum when positioned in the prepared ligament tunnel end, and will fully extend when a tensile force is applied to the graft, as illustrated in FIGS. 12 and 13. Accordingly, pins 16 or at least their individual mounting to disk 11, are each resilient to allow for such pin flexure. In practice the pins 16 and disk 11 can be manufactured from the same or different materials, provided the selected materials meet the requirement for resiliency and are proper for human implantation. For example, the fixation device 10 can be manufacture from a Nitenol ™ steel, or the like, or from a biodegradable plastic, such as polygalactia acid, within the scope of this disclosure. Or the pins 16 can be manufactured from a plastic and the disk 11 formed from metal or vice versa, within the scope of this disclosure. Which mountings and barbs or pins of the other embodiments as set out below, should be understood, to be likewise formed.

Figure 2:
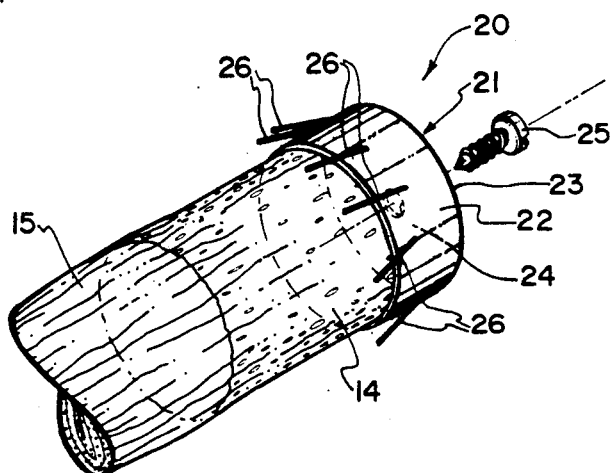
FIG. 2 is a view like that of FIG. 1 only showing a second embodiment of the endosteal ligament fixation device as a cap that is secured over the bone end with a number of spaced barbs or pins shown extending radially therefrom that are set off from and above the bone surface.

FIG. 2 shows another or second embodiment of the fixation device 20 that is also shown fitted to the bone end 14 tendon 15 connected thereto. Fixation device 20 is shown as a crown or cap 21 having a cylindrical side wall 22, with a flat top 23 thereacross. A center hole 24 is shown in broken lines formed through the center of top 23, and a screw 25 is shown aligned with that hole 24 for turning into the top surface of bone end 14, securing the cap 21 thereto. Pins 26, that, it should be understood, are like pins 16 of fixation device 10, are equidistantly spaced and extend radially from around the side wall 22, and are angled outwardly so as to be offset from that bone end 14 surface. The fixation devices 10 and 20 are essentially identical to one another as to their manufacture and use.

Figure 3:
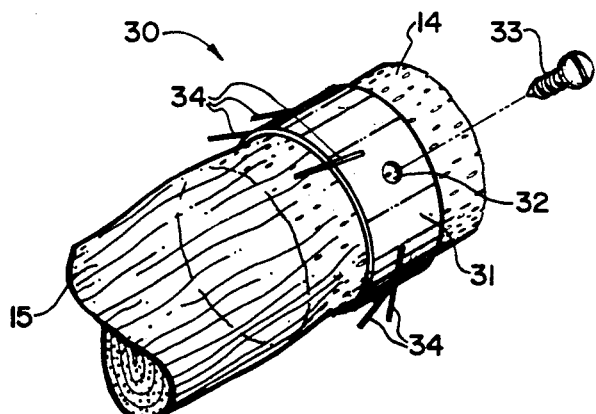
FIG. 3 is a view like that of FIG. 1 only showing a third embodiment of the endosteal ligament fixation device as a collar that is secured by a screw type fastener around the bone end wherefrom a number of spaced barbs or pins extend radially that are offset from and extend above the bone end surface.

In FIG. 3 is shown still another or third embodiment of fixation device 30, that is shown as a ring or band 31 that is fitted over the bone end 14 end and is slid therealong to approximately a mid-point. The band 31 is shown holed at 32 and shows a screw fastener 33 aligned with that hole for turning therethrough and into the side of bone end 14. Of course, more than one such hole and screw fastener can be employed for mounting the fixation device. The fixation device 30, like fixation devices 10 and 20, includes pins 34 that project radially outwardly from around the ring or band surface, and are angled therefrom rearwardly to extend over and are spaced apart from the bone 14 end surface.

Figure 4:
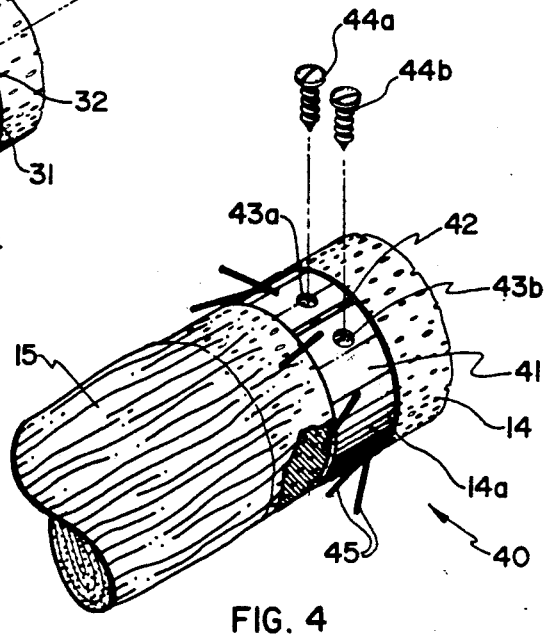
FIG. 4 is a view like that of FIG. 3 only showing the bone end as having been grooved and with the endosteal ligament fixation device collar broken and fitted therearound as a belt with fasteners shown securing it to that bone end.

FIG. 4 shows still another or fourth embodiment of the present invention in a fixation device 40. Fixation device 40 includes a ring or band 41 that is like the ring or band 31 of FIG. 3, except that it is broken at 42 into a belt and is holed proximate to the belt ends at 43a and 43b, respectively. Which holes 43a and 43b receive screw fasteners 44a and 44b, turned therein for maintaining the broken ring or band 41 around the bone end 14. While the ring or band ends are shown in FIG. 4, arranged side-by-side, it should be understood, that the one belt end could overlay the other and a plurality of spaced holes for receiving fasteners could be formed through the belt ends for providing a sizing capability. Like the fixation device 30 of FIG. 3, fixation device 40 of FIG. 4 also includes barbs or pins 45 that extend at spaced intervals therefrom so as to point rearwardly towards the tendon 15, and are spaced off from the bone end 14 surface. Though, of course, as set out above, other configurations of barbs or pins can be employed within the scope of this disclosure.

Figure 5:
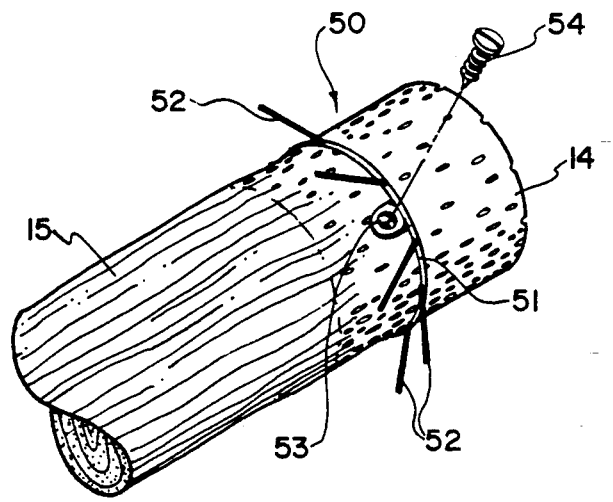
FIG. 5 is a view like that of FIG. 3 only showing a fourth embodiment of the endosteal ligament fixation device as a thin ring that is fitted over the bone end and is secured thereto, against rotation, by a fastener fitted through a tab portion and includes a plurality of spaced barbs or pins extending radially therefrom.

FIG. 5 shows yet another or fifth embodiment of a fixation device 50 of the invention that, it should be understood, functions essentially like the fixation devices of FIGS. 1 through 4, as described above. Distinct from the fixation devices of FIGS. 1 through 4, however, fixation device 50 is formed as a single narrow band or ring 51 wherefrom a number of barbs or pins 52 extend radially and rearwardly so as to be offset from the surface of bone end 14. The narrow ring or band with barbs or pins extending therefrom is preferably formed as a unit from an appropriate material such that, the barbs or pins 52 are resilient, functioning as described above. A tab 53 is also formed to extend from and in the plane of the undersurface of the narrow band or ring to extend rearwardly from and lie on the bone end 14 surface. Which tab 53 is shown as holed to receive a screw fastener 54 turned therethrough into the bone end 14. Where only one tab 53 and screw fastener 54 is shown, it should be understood, that at least a pair of spaced tabs 53 and the screw fasteners 54 for fitting therethrough are preferred. The tabs and fasteners to both position the fixation device 50 onto the bone end 14 and to prohibit rotation of the ring or band as could cause the pins 52 to rotate over the band or ring 51 to where they point forwardly, towards the bone end face. In which configuration, the barbs or pins would tend to bend or flex forward to release the graft responsive to an application of a tensile force to that graft, thereby freeing it.

Figure 6:
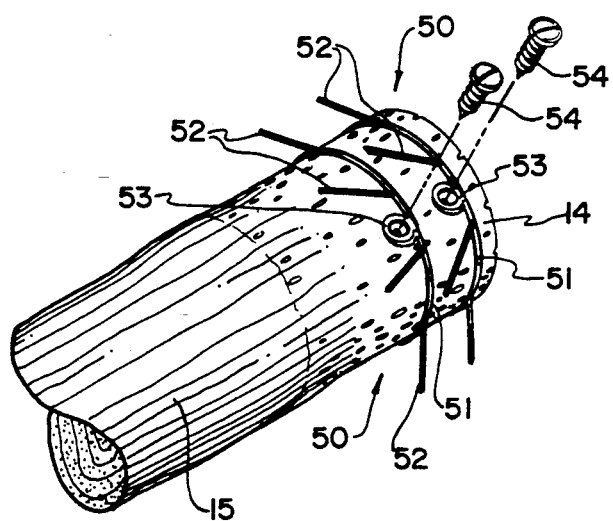
FIG. 6 is a view of a bone like that of FIGS. 1 through 3, only showing a pair of the narrow ring endosteal fixation devices of FIG. 5 fitted therearound.
Figure 7:
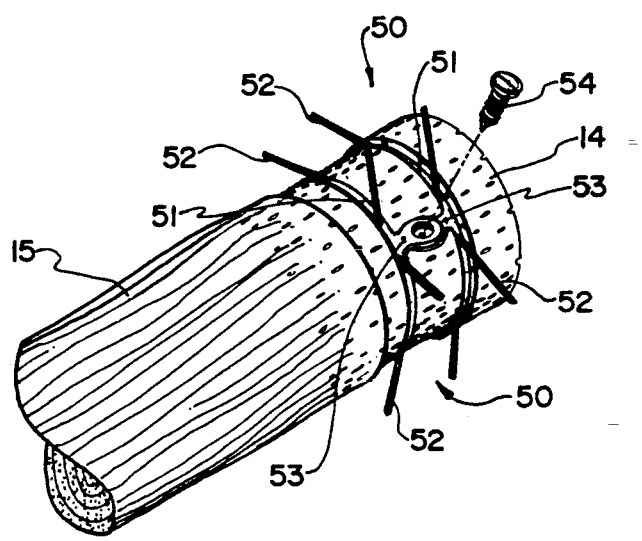
FIG. 7 is a view like that of FIG. 4 only showing two of the endosteal ligament fixation devices of FIG. 5 arranged in a groove formed around the bone end and are secured thereto by a single screw fastener fitting through overlaying tabs.

FIG. 6 shows a pair of fixation devices 50 of FIG. 5 that are secured in parallel or stacked arrangement around the bone end 14, functioning as described above. In FIG. 7 is also shown a pair of stacked fixation devices 50 that are essentially like those shown in FIGS. 5 and 6, except that the respective tabs 53 of each are formed to face oppositely, for overlaying one another. The holes in which overlayed tabs 53 align and are to receive a single screw fastener 54 for maintaining both fixation devices 50 to the bone end. Also, fixation devices 50 are shown seated in a grooved section of bone end 14. Which grooved section lower wall terminates below the lowest fixation device 50 so as to allow for flexing of the fixation device barbs or pins 52 into engagement with the bone end 14 surface during graft installation, as set out below.

Figure 8:
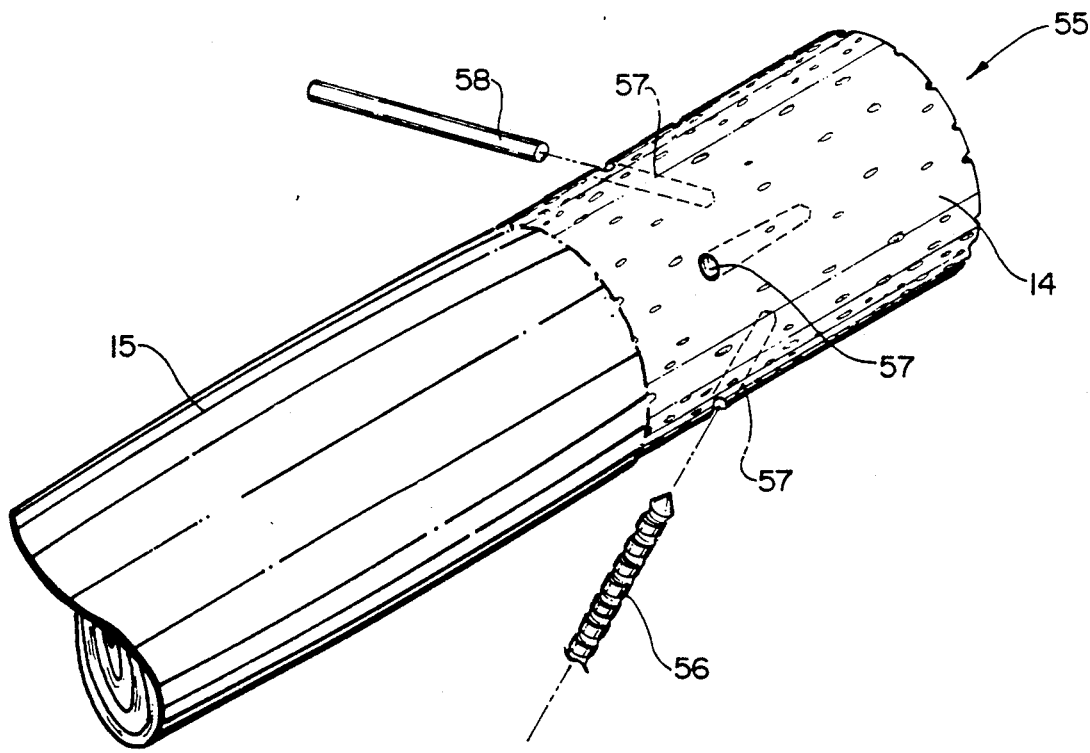
FIG. 8 is still another or sixth embodiment of the endosteal ligament fixation device where the mounting is a plurality of spaced slanted holes formed into the graft bone end, each for receiving a barb or pin secured therein.

FIG. 8 shows yet another fixation device 55 being formed by individually mounting pins 58 to and at an angle rearwardly from the bone end 14. Shown therein, a plurality of spaced slanted holes 57 are drilled, as with a drill bit 56, into the graft bone end 14. Four slanted holes 57 are shown drilled at compass points around the bone end, though a minimum of two such slanted holes could be so drilled, or otherwise formed. The slanted holes 57 are each to receive pins 58 fitted and secured therein, within the scope of this disclosure. The pins 58, as shown in FIGS. 8 and 9, are preferably each of sufficient thickness, length and strength to withstand displacement at a tensile stress as it is estimated the graft could experience after installation, which anticipated load is anticipated to be a maximum of approximately eighty (80) pounds.

Figure 9:
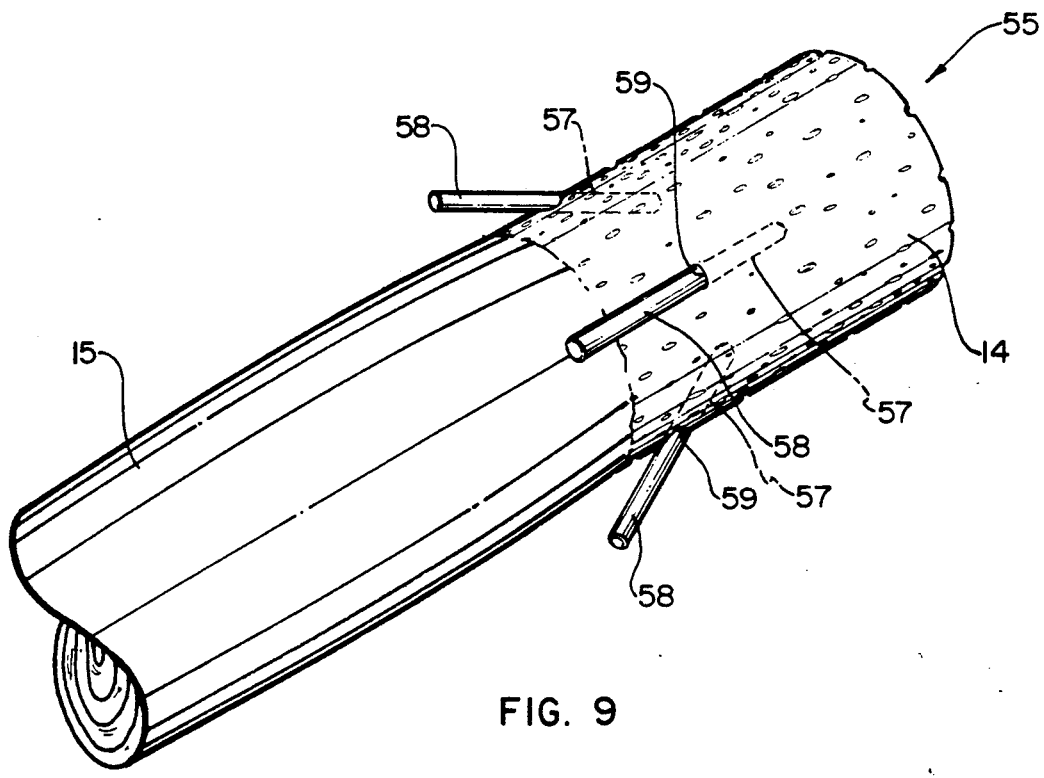
FIG. 9 is a view like FIG. 8, showing the barbs or pins secured in the bone end slanted holes.

FIG. 9 shows the pins 58 seated in holes 57 and maintained therein as by an application of an adhesive 59. So arranged, the fixation device 55 functions to mount the graft bone end 14 in the bone endosteum as shown in FIGS. 12 and 13 and as discussed hereinbelow.

It should be understood that the barbs or pins of the fixation devices of the invention can be pointed or blunt, or the ends thereof can be otherwise shaped as into hooks or half hooks, not shown, or can be formed into a spoon or blade, or the like, not shown, all within the scope of this disclosure. The barbs or the pins of all the fixation device embodiments are for flexing into for securely maintaining each fixation device in the bone endosteum, as illustrated in FIGS. 12 and 13, when a tensile force is applied to the graft. Accordingly, it should be understood, that any configuration of barbs or pins and their ends with the fixation device body arranged to further promote fixation device stability, will fall within the scope of this invention.

Hereinabove has been set our six embodiments of endosteal fixation devices of the present invention. Common to all is a mounting of barbs or pins either into the bone end or in a mount for fitting to, or encircling the bone end of a bone tendon graft for installation as a replacement ligament in a knee arthroscopic surgical procedure. Also common to all the fixation device embodiments are a plurality of barbs or pins which plurality can be as few as a pair, that extend radially outwardly from around the bone end 14 and are preferably spaced equidistantly. Which barbs or pins, however, within the scope of this disclosure may be of different thickness, length and strength and may even be at different angles so long as the pin arrangement exhibits sufficient strength to maintain the bone end in the endosteum with application of a tensile force thereto as the knee experiences during use. The barbs or pins all slope rearwardly towards the tendon 15 and, in a relaxed state, are offset from that bone end surface. During installation of which bone tendon bone graft in a prepared ligament tunnel, as shown in FIGS. 10 and 11, the resilient barbs or pins flex into engagement with the bone end surface. Which barbs or pins will spring outwardly into the bone endosteum when a force urging the graft into the prepared ligament tunnel is terminated, thereby permanently seating the graft bone end in the tunnel bone endosteum. To provide such barb or pin flexure all are formed from a flexible or flexing material. Which material may be absorbable by the human body, as for example, a plastic such as polygalactia acid, or may be a human body compatible material, such as Nitenol TM steel, or the like.

As set out hereinabove, the disk, collar, ring or band mounting and barbs or pins can be cast or otherwise formed as a unit, or can be separately installed to the mounting. Which barbs or pins can also be individually installed directly into the bone end, as shown in FIGS. 8 and 9. Such installation can involve drilling the disk, collar, ring, band or bone end at intervals and at angles to the surface thereof to provide, when each barb or pin is seated and secured therein, as by soldering, application of an adhesive, or the like, which mounting must be such that the barbs or pins project rearwardly at an angle of less than sixty (60) degrees relative to bone end 14, spaced above the plane of the mounting surface. Which angle, as set out hereinabove is, in practice, preferably approximately a thirty (30) degree angle for each barb or pin.

FIGS. 10 through 13 show a utilization of the fixation device 30 to secure the bone end 14 in a prepared ligament tunnel 63. Which ligament tunnel is formed from the tibia 62 cortex, at its tuberosity, through tibia 62, and the points of ligament origin of the anterior cruciate ligament, and into the femur 61, terminating in the femur endosteum 64. Fixation device 30 of FIG. 3, is shown in FIGS. 10 through 13, as mounted to the graft bone end 14. Though, it should, be understood, fixation device 30 is shown by way of example, and that any of the described fixation device embodiments could be so utilized within the scope of this disclosure.

FIGS. 10 and 11, show the bone end 14 with fixation device 30 mounted thereto being urged into the femoral knee junction end of ligament tunnel 63. The barbs or pins 34 of fixation device 30 are shown depressed into engagement with the bone end 14 surface by the passage along the wall of tunnel 63. Such urging can be provided by a surgeon fitting a straight driver tool, not shown, longitudinally into ligament 15, the end thereof butting against the undersurface of bone end 14, and manually pushing that bone end 14 and anchor 30 into the ligament tunnel 63. Or, within the scope of this disclosure, another appropriate surgical technique can be utilized to fit the graft bone end, such as fitting a K-wire through the femur cortex to intersect the ligament tunnel end and coupling it to the bone end 14 for pulling. Or, a suture or sutures can be connected to the bone end after capture by such K-wire and the sutures used to pull the fixation device 30 fully into the ligament tunnel, as shown in FIGS. 12 and 13.

FIGS. 12 and 13 show the ligament graft fully installed in the ligament tunnel 63, that tunnel shown as ending in the femur endosteum 64. With the graft so installed, and the force urging it into the ligament tunnel discontinued, the barbs or pins 34 will flex or flare outwardly into the bone endosteum 64, as shown. Thereafter, upon application of a tensile force to the tendon 15, the barbs or pins 34 will fully extend to their limit of outward flexure, locking the fixation device 30 and graft bone end 14 in place.

In practice, the limit of barb or pin rotation is preferably to approximately an angle of thirty (30) degrees from the surface of bone end 14, but can be within a range of angles of from ten (10) to sixty (60) degrees, within the scope of this disclosure. Which barb or pin 34 rotation, however, as set out hereinabove, cannot pass a right angle to the bone end 14 surface without the barbs or pins releasing from the bone endosteum, releasing also the graft. In a practice of the invention, the barbs or pins are selected and their number and arrangement is determined to provide sufficient pull-out strength to withstand a tensile force as could be anticipated to be applied to the ligament to a maximum of approximately eighty (80) pounds, and should individually be able to withstand an applied force of twenty (20) pounds without failure. Which barbs or pins are preferably from one and one-half (1½) to three (3) millimeters in length.

Hereinabove has been set out an endosteal ligament fixation device for use with a bone tendon bone ligament graft. The graft of FIGS. 12 and 13, however, is shown as a bone tendon graft with the bone end 14 secured in the femur endosteum 64 and the tendon 15 end shown secured by a staple 65 onto the tibial cortex surface, adjacent to the ligament tunnel end. In this configuration, the other graft bone end has been removed and the tendon 15 is fixed as the graft end to the tibial cortex. It should, however, be understood, that a bone end of which graft can be secured in the tibial portion of ligament tunnel, as with a set screw. Or can be otherwise secured in any appropriate like manner, within the scope of this disclosure.

Applicant has hereinabove set out a number of embodiments of endosteal ligament fixation devices of the present invention and has detailed their functioning for mounting a bone end of a bone tendon bone graft as a replacement ligament in the knee cruciate ligament replacement surgical procedure. Therefore, while preferred forms of the invention have been shown and described herein, it should be understood that the invention may be embodied in other arrangements within the scope and spirit of this disclosure. The present disclosure should therefore be considered to be presented for illustration, and is made by way of example only, and that variations thereto are possible without departing from the subject matter and reasonable equivalency thereof, coming with the scope of the following claims, which claims I regard as my invention.

I claim:

1. An endosteal fixation device comprising, a mounting means including a plurality of pin means to extend outwardly from around a graft; said plurality of pin means are spaced equidistantly and extend radially outwardly and rearwardly from said mounting means, each at an angle less than sixty (60) degrees of from said graft surface, said pin means each formed to flex toward said graft surface when compressed during travel within a bone tunnel or hole and will spring outwardly to their original altitude when that compression is released so as to lock into the bone endosteum wherein said bone tunnel or hole is formed.

2. An endosteal fixation device as recited in claim 1, wherein the mounting means are slanted holes that are formed at equidistant intervals into the graft end, each for receiving and maintaining an individual pin means therein.

3. An endosteal fixation device as recited in claim 2, wherein the means for securing is an adhesive coating of the pin means end for installation in a slanted hole.

4. An endosteal fixation device as recited in claim 1, wherein the mounting means is a disk for fitting across the end face of the graft end, which disk has a hole formed through its center; and the means for securing is a screw type fastener for turning through said disk center hole and longitudinally into said graft end.

5. An endosteal fixation device as recited in claim 1, wherein the mounting means is a cap for fitting over the end surface of the graft end, which cap has a hole formed through its center; and the means for securing is a screw type fastener for turning through said cap center hole and longitudinally into said graft end.

6. An endosteal fixation device as recited in claim 1, wherein the mounting means is a band for fitting around the surface of the graft end, which band is holed therethrough; and a screw type fastener for turning through said band hole into said graft end.

7. An endosteal fixation device as recited in claim 6, wherein the band is broken laterally, to allow the band ends to move together to cinch around the surface of the graft end, which band is holed at its ends; and screw type fasteners for turning through said belt end holes into said graft end.

8. An endosteal fixation device as recited in claim 1, wherein the barbs or pins are individually spaced off from the graft end surface, each at approximately thirty (30) degrees.

9. An endosteal fixation device as recited in claim 1, wherein the mounting means is a narrow ring with the pin means formed therewith.

10. An endosteal fixation device as recited in claim 9, wherein the pin means are barbs or pins that are formed with the narrow ring; and the mounting means are tabs, that are each holed therethrough and are formed to extend from and in the plane of the bottom of the narrow ring, to extend over the graft end surface.

11. An endosteal fixation device as recited in claim 10, wherein a pair of narrow rings with pin means formed therewith are for installation to the graft end surface, the tabs of one facing oppositely to the other to overlay one another, for receiving a single screw type fastener through each set of overlaid tabs.

12. An endosteal fixation device as recited in claim 1, wherein the pin means is formed from a resilient material.

13. An endosteal fixation device as recited in claim 12, wherein the resilient material is a biodegradable material.

14. An endosteal fixation device as recited in claim 11; wherein the resilient material is a biocompatible steel.

15. An endosteal fixation device as recited in claim 1, wherein the mounting means and pin means are formed from the same resilient material.

* * * * *